(12) United States Patent
Lee et al.

(10) Patent No.: US 12,011,223 B2
(45) Date of Patent: Jun. 18, 2024

(54) EYE PHANTOM FOR EVALUATING RETINAL ANGIOGRAPHY IMAGE

(71) Applicant: Korea Research Institute of Standards and Science, Daejeon (KR)

(72) Inventors: Sang Won Lee, Sejong-si (KR); Il Doh, Daejeon (KR); Hyunji Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 595 days.

(21) Appl. No.: 17/280,284

(22) PCT Filed: Oct. 8, 2019

(86) PCT No.: PCT/KR2019/013198
§ 371 (c)(1),
(2) Date: Mar. 26, 2021

(87) PCT Pub. No.: WO2020/153575
PCT Pub. Date: Jul. 30, 2020

(65) Prior Publication Data
US 2022/0000356 A1    Jan. 6, 2022

(30) Foreign Application Priority Data
Jan. 23, 2019 (KR) .................. 10-2019-0008743

(51) Int. Cl.
*A61B 3/00* (2006.01)
*A61B 3/10* (2006.01)
*A61B 3/12* (2006.01)

(52) U.S. Cl.
CPC ............ *A61B 3/0025* (2013.01); *A61B 3/102* (2013.01); *A61B 3/1241* (2013.01)

(58) Field of Classification Search
CPC ..... A61B 3/0025; A61B 3/102; A61B 3/1241; A61B 3/00; G09B 23/303; G09B 23/286
(Continued)

(56) References Cited

U.S. PATENT DOCUMENTS

| 2005/0049578 A1* | 3/2005 | Tu ........................... A61B 3/16 |
| | | 977/956 |
| 2007/0049987 A1* | 3/2007 | Greenberg .......... H05K 1/0281 |
| | | 607/54 |

(Continued)

FOREIGN PATENT DOCUMENTS

CN    107736872 A    2/2018

OTHER PUBLICATIONS

Baxi et al., "Retina-simulating phantom for optical coherence tomography", Journal of Biomedical Optics, Feb. 2014, pp. 1-8, vol. 19(2), SPIEDigitalLibrary.org/jbo.
(Continued)

*Primary Examiner* — Mohammed A Hasan
(74) *Attorney, Agent, or Firm* — The Webb Law Firm

(57) ABSTRACT

The present invention relates to an eye phantom for evaluating a retinal angiography image, and a manufacturing method therefor. A purpose of the present invention is to provide an eye phantom for evaluating a retinal angiography image, capable of simulating even the vascular structure and blood flow of a retina so as to be more similar to an actual retinal structure than a conventional eye phantom; and a manufacturing method therefor. More specifically, a purpose of the present invention is to provide an eye phantom for evaluating a retinal angiography image, including various shapes of fine fluid channel structures corresponding to the vascular structure formed in an actual retina; and a manufacturing method therefor.

26 Claims, 13 Drawing Sheets

(58) Field of Classification Search
USPC .......................................................... 351/205
See application file for complete search history.

(56) References Cited

U.S. PATENT DOCUMENTS

| | | | |
|---|---|---|---|
| 2009/0240124 A1* | 9/2009 | Hefti ................. | A61B 5/14532 |
| | | | 600/319 |
| 2011/0181836 A1* | 7/2011 | Rowe .................... | G09B 23/34 |
| | | | 351/205 |
| 2016/0189570 A1* | 6/2016 | Dong .................... | G09B 23/30 |
| | | | 434/271 |
| 2016/0278637 A1* | 9/2016 | Gao ......................... | A61B 3/14 |
| 2016/0291217 A1 | 10/2016 | Furukawa et al. | |
| 2017/0042730 A1* | 2/2017 | He .......................... | A61B 34/30 |

OTHER PUBLICATIONS

Hayakawa et al., "Retinal vessel model fabricated on a curved surface structure for a simulation of microcannulation", ROBOMECH Journal, 2016, pp. 1-8, vol. 3:19, SpringerOpen.

Lemaillet et al., "Dynamic eye phantom for retinal oximetry measurements", Journal of Biomedical Optics, Nov./Dec. 2009, pp. 1-6, vol. 14(6), Society of Photo-Optical Instrumentation Engineers.

* cited by examiner

NFL: nerve fiber layer
GCL: ganglion cell layer
IPL: inner plexiform layer
INL: inner nuclear layer
OPL: outer plexiform layer
ONL: outer nuclear layer

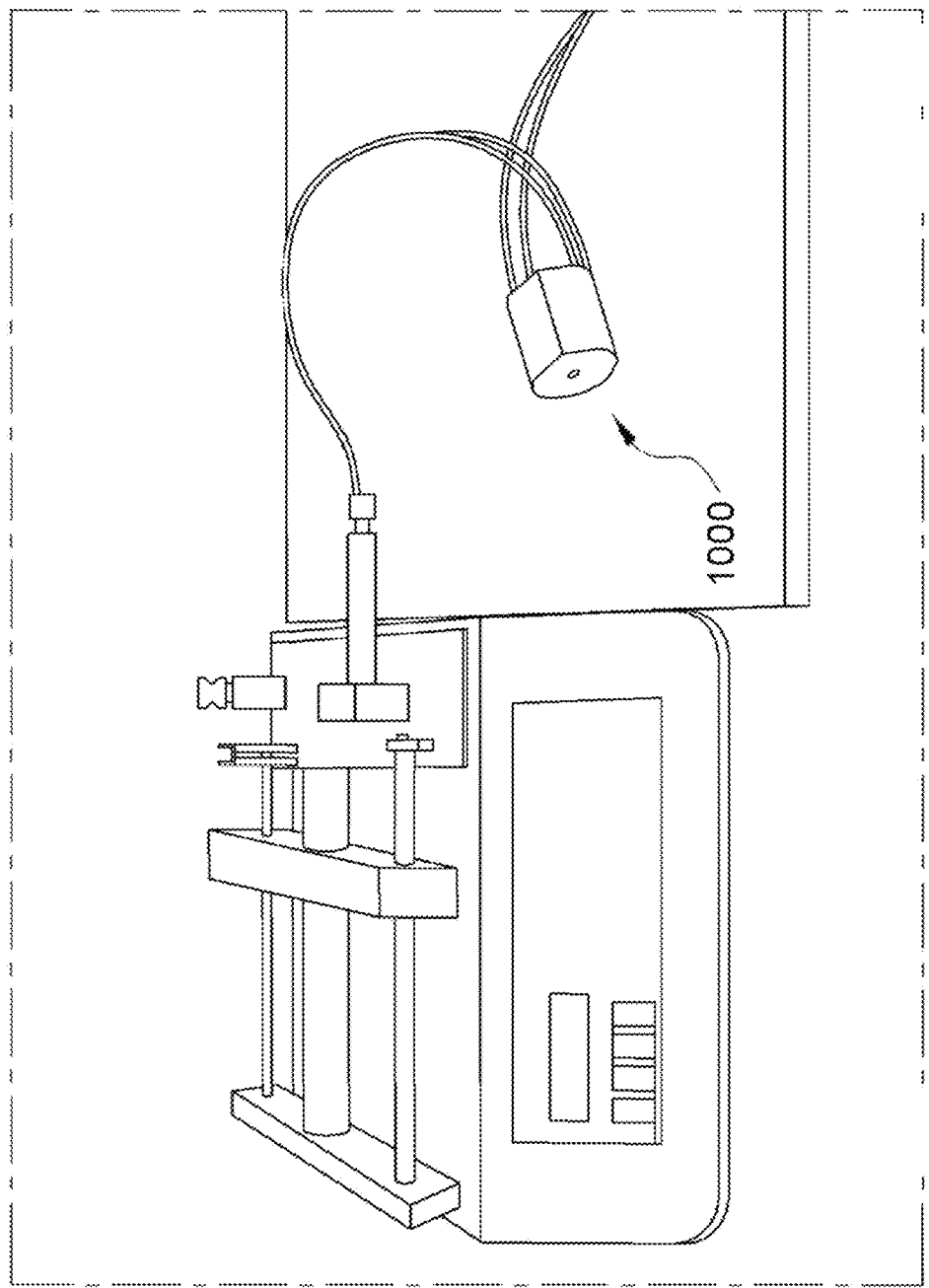

EYE PHANTOM FOR EVALUATING RETINAL ANGIOGRAPHY IMAGE

CROSS-REFERENCE TO RELATED APPLICATIONS

This application is the United States national phase of International Application No. PCT/KR2019/013198 filed Oct. 8, 2019, and claims priority to Korean Patent Application No. 10-2019-0008743 filed Jan. 23, 2019, the disclosures of which are hereby incorporated by reference in their entirety.

BACKGROUND OF THE INVENTION

Field of the Invention

The present invention relates to an eye phantom for evaluating a retinal angiography image, and more particularly, to an eye phantom for evaluating a retinal angiography image which is used to evaluate an optical coherence tomography (OCT) for ophthalmology that photographs an image to observe a retina of an eyeball or the like, and can more easily and smoothly perform a performance evaluation of the OCT by simulating an actual structure of the eyeball more similarly.

Description of Related Art

A retina of a human eye is a core tissue that detects light and determines vision, and is a very thin tissue with a thickness of less than 0.5 mm, and cannot be repaired once damaged. Therefore, observing the retina in eye disease to correctly and accurately point out a lesion is considered a very important factor in the treatment of the disease. As representative retina tomography equipment for diagnosing such eye diseases and checking treatment progress, there is optical coherence tomography (OCT) for ophthalmology.

Most of the retina OCTs currently used in practical sites such as a hospital are a fourth generation OCT product (SD-OCT), and has a much higher quality of image compared to the previous generation equipment and can acquire images of a 3D cross-sectional structure of a retina. The OCT makes it possible to perform diagnosis or monitoring of treatment progress by visually checking a morphological change of the retina or measuring a thickness in a specific area. Recently, a fifth generation OCT product (OCT-A) equipped with a function of acquiring angiography images from OCT images without contrast agents has been released after approval from the US Food and Drug Administration (FDA) in 2015.

The market for ophthalmic diagnostic devices currently stands at about 1.4 billion USD worldwide, and it is known that the OCT-related market is the largest among the ophthalmic diagnostic devices. However, Korea currently imports almost all of the equipment from overseas companies such as the United States, Germany and Japan, and it has been pointed out that the domestic OCT technology field is too dependent on foreign technology. Therefore, research and development efforts to develop domestic OCT equipment are being made steadily.

However, there are the following problems in developing domestic OCT equipment. In the case of the OCT for ophthalmology domestically imported, only electric/electromagnetic stability evaluation and laser stability evaluation are made, and the performance evaluation of the actual equipment, that is, the evaluation on how accurately retina images are observed is not separately made upon import. That is, there is a problem in that it is still difficult to perform the systematic evaluation on the OCT equipment in Korea, and the process of checking and improving performance in the process of developing domestic OCT equipment is not smoothly performed. Specifically, in order to obtain medical device certification after the development of the medical device product is completed, evaluation through preclinical or clinical trials is necessarily conducted. However, since it is impossible to conduct tests on animals or humans in the process of product development or in the process of performance evaluation and production for obtaining medical device certification, it is very difficult to realize performance verification and improvement work in the equipment development process.

Of course, in order to solve such a problem in the prior art, instead of using an eyeball of an actual animal or human, a technique of acquiring an image and evaluating the performance using an eye phantom simulating the eyeball has been used. The eye phantom for evaluating the performance of the conventional OCT equipment includes a multilayer film structure in which several layers are stacked by simulating a structure of a retina tissue. The structure of the eye phantom conventionally used is disclosed in the paper "Retina-simulating phantom for optical coherence tomography" (Jigesh Baxi et al., Journal of Biomedical Optics 19(2), 021106, February 2014, hereinafter 'Prior Document 1'), Chinese Patent Publication No. 107736872 ("Human eye phantom for eyeground tomography and OCT imaging quality evaluation method", Feb. 27, 2018, hereinafter 'Prior Document 2'), or the like.

However, as described above, the fifth generation OCT has a function of obtaining an angiography image from an OCT image, and it is known that the domestic OCT equipment is also being developed to realize this function. However, the conventional eye phantom as disclosed in Prior Documents 1 and 2, etc., merely simulates the multilayer film structure of the retina, and therefore has no structure corresponding to blood vessels formed in the retina. Therefore, it is impossible to obtain an image corresponding to an angiography image from an OCT image of a conventional eye phantom, and there is a problem in that there is a limitation in applying the conventional eye phantom to the development of the fifth generation OCT.

PRIOR ART DOCUMENT

Patent Document

1. Chinese Patent Publication No. 107736872 (Human eye phantom for eyeground tomography and OCT imaging quality evaluation method", 2018.02.27.)

Non-Patent Document

1. "Retina-simulating phantom for optical coherence tomography" (Jigesh Baxi et al., Journal of Biomedical Optics 19(2), 021106, February 2014)

SUMMARY OF THE INVENTION

The present invention has been devised to solve the problems of the prior art as described above, and an object of the present invention is to provide an eye phantom for evaluating a retinal angiography image, capable of simulating a vascular structure and a blood flow of a retina more similarly to an actual retinal structure compared to the conventional eye phantom, and a manufacturing method therefor. More specifically, an object of the present invention is to provide an eye phantom for evaluating a retinal angiography image, comprising various shapes of fine fluid channel structures corresponding to a vascular structure formed in an actual retina, and a manufacturing method therefor.

In one general aspect, an eye phantom 1000 may include: a retina simulating part 1100, the retina simulating part including a multilayer film structure part 1110 that is formed in a shape in which multiple layers with different scattering coefficients are stacked to simulate a multilayer cell layer structure of a retina, and a vascular layer structure part 1120 that includes a fine flow channel to simulate a vascular structure of the retina and is coupled to an upper surface and a lower surface of the multilayer film structure part 1110.

The vascular layer structure part 1120 may include: a nerve fiber layer (NFL) simulating part 1121 that is coupled to the upper surface of the multilayer film structure part by forming an NFL channel part 1121c in a form of the fine flow channel on the lower surface thereof to simulate the NFL of the vascular structure of the retina, and an outer plexiform layer (OPL) simulating part 1122 that is coupled to the lower surface of the multilayer film structure part 1110 by forming an OPL channel part 1122c in the form of the fine flow channel on the upper surface thereof to simulate the OPL of the vascular structure of the retina.

The vascular layer structure part 1120 may be formed so that a width of the NFL channel part 112c is formed larger than that of the OPL channel part 1122c to simulate that a blood vessel inside an eyeball is formed thicker than that outside the eyeball in the vascular structure of the retina. More specifically, the NFL channel part 1121c may have a width within a range of 100 to 200 μm. In addition, the OPL channel part 1122c may have a width within a range of 10 to 50 μm.

The vascular layer structure part 1120 may include: an NFL flow passage part 1121p that communicates with the NFL channel part 1121c to circulate a blood simulating fluid through the NFL channel part 1121c and is formed in a form of a through passage penetrating through the NFL simulating part 1121, and an OPL flow passage part 1122p that communicates with the OPL channel part 1122c to circulate the blood simulating fluid to the OPL channel part 1122c and is formed in a form of a through passage penetrating through the OPL simulating part 1122.

The multilayer film structure part 1110 may be formed in a shape in which a ganglion cell layer (GCL) simulating part 1111 that is formed in a form of a film having a scattering coefficient corresponding to GCL to simulate the GCL of a retinal cell layer, an inner plexiform layer (IPL) simulating part 1112 that is formed in a form of a film having a scattering coefficient corresponding to IPL to simulate the IPL of the retinal cell layer, and an inner nuclear layer (INL) simulating part 1113 that is formed in a form of a film having a scattering coefficient corresponding to INL to simulate the IPL of the retinal cell layer are sequentially stacked.

The multilayer film structure part 1110 may include: a GCL flow passage part 1111p that is formed in a form of a through passage penetrating through the GCL simulating part 1111 to circulate a blood simulating fluid to the vascular layer structure parts 1120 provided on each of the upper and lower surfaces of the multilayer film structure part 1110; an IPL flow passage part 1112p that is formed in a form of a through passage penetrating through the IPL simulating part 1112 to circulate a blood simulating fluid to the vascular layer structure parts 1120 provided on each of the upper and lower surfaces of the multilayer film structure part 1110; and an INL flow passage part 1113p that is formed in a form of a through passage penetrating through the INL simulating part 1113 to circulate a blood simulating fluid to the vascular layer structure parts provided on each of the upper and lower surfaces of the multilayer film structure part 1110.

The retina simulating part 1100 may further include an outer film structure part 1150 that is further coupled to a lower surface of the vascular layer structure part 1120 coupled to the lower surface of the multilayer film structure part to simulate an outer cell layer structure of the retina. In this case, the outer film structure part 1150 may be formed in a shape in which an outer nuclear layer (ONL) simulating part 1151 that is formed in a form of a film having a scattering coefficient corresponding to ONL to simulate the ONL of the retinal cell layer, and an outer segment simulating part 1152 that is formed in a form of a film having a scattering coefficient corresponding to an outer segment to simulate the outer segment of the retinal cell layer are sequentially stacked. In addition, the outer film structure part 1150 may include: an ONL flow passage part that is formed in a form of a through passage penetrating through the ONL simulating part 1151 to circulate a blood simulating fluid to the vascular layer structure part 1120; and an outer segment flow passage part that is formed in a form of a through passage penetrating through the outer segment simulating part 1152 to circulate the blood simulating fluid to the vascular layer structure part 1120.

The retina simulating part 1100 may further include: a multilayer film flow passage part 1110p that is formed on the multilayer film structure part 1110 in a form of a through passage penetrating through the multilayer film structure part 1110 to circulate a blood simulating fluid and a blood vessel layer flow passage part 1120p that is formed on the vascular layer structure part 1120 in a form of a through passage communicating with the fine flow channel and the multilayer film flow passage part and penetrating through the vascular layer structure part; a flow passage part 1130 that inflows or discharges a blood simulating fluid by being formed in a form of a tube connected to the blood vessel layer flow passage part 1120p formed on a lower surface of the retina simulating part 1100 to circulate the blood simulating fluid to the fine flow channel; and a sealing part 1140 that is formed in a form of a stopper that seals the blood vessel layer flow passage part 1120p formed on an upper surface of the retina simulating part 1100 to prevent the blood simulating fluid from leaking the retina simulating part 1100.

The retina simulating part 1100 may further include: an outer film structure part 1150 that is further coupled to a lower surface of the vascular layer structure part 1120 coupled to the lower surface of the multilayer film structure part 1110 to simulate an outer cell layer structure of the retina. In this case, an outer film flow passage part formed in a form of a through passage penetrating through the outer film structure part 1150 may be formed in the outer film structure part 1150 to circulate a blood simulating fluid, and the flow passage part 1130 may communicate with the blood vessel layer flow passage part 1120p through the outer film flow passage part.

The eye phantom 1000 may further include: a lens part 1200 that includes at least one lens to simulate a crystalline lens of an eyeball; the retina simulating part 1100 that is spaced apart from the lens part 1200 so that an upper surface faces toward the lens part 1200 on an axis of the lens part 1200; and a housing part 1300 that has the lens part 1200 supported on one side thereof and the retina simulating part 1100 supported on the other side thereof. An accommodation space 1300V in which a vitreous body simulation fluid is accommodated may be formed between the lens part 1200 and the retina simulating part 1100 in the housing part 1300 to simulate a vitreous body of the eyeball. The eye phantom 1000 may further include: a flow rate control unit that is provided in the flow passage part 1130 to control a flow rate of the blood simulating fluid that flows into and is discharged from the retina simulating part 1100.

According to a manufacturing method of an eye phantom for evaluating a retinal angiography image of the present invention, a manufacturing method of the eye phantom 1000 as described above for manufacturing the vascular layer structure part 1120 may include: irradiating etching light onto an upper surface of a wafer through a mask having a reverse pattern shape of the fine flow channel shape; forming a reverse pattern on the upper surface of the wafer by etching and removing the light irradiated portion on the wafer; inputting a blood vessel layer raw material, which is a raw material of the vascular layer structure part 1120, into the reverse pattern; stacking and pressing a substrate on an upper surface of the blood vessel layer raw material input into the reverse pattern; separating, from the wafer, the blood vessel layer raw material cured in a state in which a pattern having a reverse shape to the reverse pattern is formed on a lower surface of the blood vessel layer raw material, and the upper surface thereof adheres to the substrate; and separating the blood vessel layer raw material on which the fine flow channel pattern is formed from the substrate.

The manufacturing method of the eye phantom 1000 may further include: before the stacking and pressing of the substrate, coating a coating agent on a lower surface of the substrate to easily separate the blood vessel layer raw material from the substrate in the separating of the blood vessel layer raw material from the substrate.

The manufacturing method of the eye phantom 1000 may further include: after the separating of the blood vessel layer raw material from the substrate, cutting and removing an extra portion of the blood vessel layer raw material on which the fine flow channel pattern is formed.

The blood vessel layer raw material may be a mixture of a curable resin and a scattering agent. More specifically, the curable resin may be polydimethylsiloxane (PDMS). In addition, the scattering agent may be $TiO_2$.

According to a manufacturing method of an eye phantom for evaluating a retinal angiography image of the present invention, a manufacturing method of the eye phantom 1000 described above for manufacturing the multilayer film structure part 1110 may include: coating a coating agent on an upper surface of a substrate; inputting a multilayer film raw material, which is a raw material of the multilayer film structure part 1110, into the upper surface of the substrate; diffusing the multilayer film raw material into the whole upper surface of the substrate by rotating the substrate; stopping the rotation of the substrate when the multilayer film raw material forms a predetermined thickness; and curing the multilayer film raw material.

The manufacturing method of the eye phantom 1000 may further include: forming a laminate of multiple layers having different scattering coefficients on the upper surface of the substrate by repeatedly forming the multilayer film the inputting of the multilayer film raw material, the diffusing of the multilayer film raw material, the stopping of the rotation of the substrate, and the curing of the film.

The multilayer film raw material may be a mixture of a curable resin and a scattering agent. More specifically, the curable resin may be polydimethylsiloxane (PDMS). In addition, the scattering agent may be $TiO_2$.

Advantageous Effects

According to the present invention, the eye phantom includes various shapes of fine fluid channel structures corresponding to the vascular structure formed in the actual retina, thereby simulating even the vascular structure and blood flow of a retina so as to be more similar to an actual retinal structure than a conventional eye phantom. Therefore, according to the present invention, the eye phantom is applied to the fifth generation OCT development process equipped with the function of acquiring the angiography image from the OCT image, thereby accurately evaluating the performance of the equipment under development. In particular, since the conventional equipment under development cannot perform the performance evaluation directly using animals or humans, there has been no method to correctly evaluate the performance, but according to the present invention, since the performance of the equipment under development can also be evaluated as described above, there is a great industrial effect that the OCT equipment can be developed much smoother. In addition, it is possible to evaluate the performance of a fluorescent blood vessel contrast fundus camera by pouring a solution containing a fluorescent substance into the fine fluid channel.

BRIEF DESCRIPTION OF THE DRAWINGS

FIG. 13 is an actual photograph of a structure of the eye phantom according to the present invention.

[Description of the Invention]

1000: Eye phantom
1100: Retina simulating part

-continued

| [Description of the Invention] | |
|---|---|
| 1110: Multilayer film structure part | 1110p: Multilayer film flow passage part |
| 1111: GCL simulating part | 1111p: GCL flow passage part |
| 1112: IPL simulating part | 1112p: IPL flow passage part |
| 1113: INL simulating part | 1113p: INL flow passage part |
| 1120: Vascular layer structure part | 1120p: Blood vessel layer flow passage part |
| 1121: NFL simulating part | |
| 1121c: NFL channel part | 1121p: NFL flow passage part |
| 1122: OPL simulating part | |
| 1122c: OPL channel part | 1122p: OPL flow passage part |
| 1130: Flow passage part | 1140: Sealing part |
| 1150: Outer film structure part | |
| 1151: ONL simulating part | 1152: Outer segment simulating part |
| 1200: Lens part | 1300: Housing part |

BEST MODE

Hereinafter, an eye phantom for evaluating a retinal angiography image and a manufacturing method therefor according to the present invention having the above-described configuration will be described in detail with reference to the accompanying drawings.

Retina Simulating Part Structure and Manufacturing Method

Figure 1A:
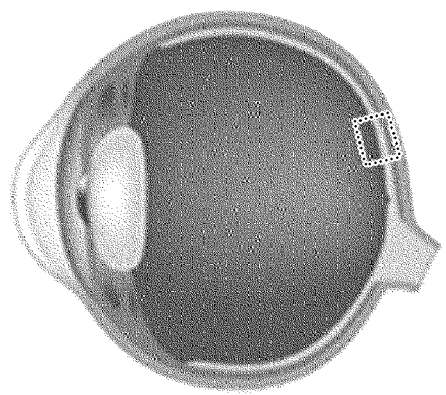
FIGS. 1A and 1B are diagrams illustrating a structure of an actual eyeball and retina tissue.
Figure 1B:
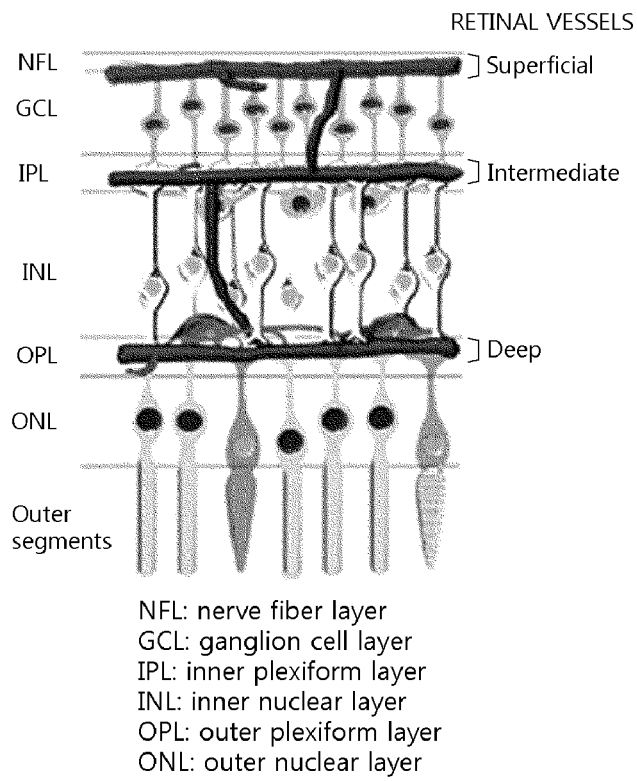

FIG. 1 illustrates a structure of an actual eyeball and retina tissue. A structure of a retina structure of FIG. 1B is an enlarged view of a portion represented by a small square in the actual eyeball of FIG. 1A. As illustrated in FIG. 1B, the retina tissue is formed in a shape in which a nerve fiber layer (NFL), a ganglion cell layer (GCL), an inner plexiform layer (IPL), an inner nuclear layer (INL), an outer plexiform layer (OPL), an outer nuclear layer (ONL), and an outer segment are sequentially stacked from an inner side to an outer side of the eyeball. As illustrated in FIG. 1B, blood vessels are distributed in a superficial NFL and a deep OPL. Some blood vessels for connecting blood vessels distributed in the NFL and blood vessels distributed in the OPL are distributed in an intermediate IPL, but most blood vessels are distributed approximately in the NFL and OPL.

As suggested in Prior Documents 1, 2, and the like, a part simulating a retina in the conventional eye phantom has merely a structure of a multilayer shape in which each layer such as NFL, GCL, . . . , OPL has different scattering coefficients. In other words, a vascular structure itself formed in the retina is not implemented at all. Accordingly, in testing the performance of the fifth generation OCT (having a function of obtaining an angiography image from an OCT image), which is recently being developed, it is impossible to obtain an angiography image without using an eyeball of an actual animal or human with blood vessels. The eye phantom according to the present invention introduces a structure, which realizes the simulation of the blood vessel, into the retina simulating part of the eye phantom to solve this problem.

Figure 2:
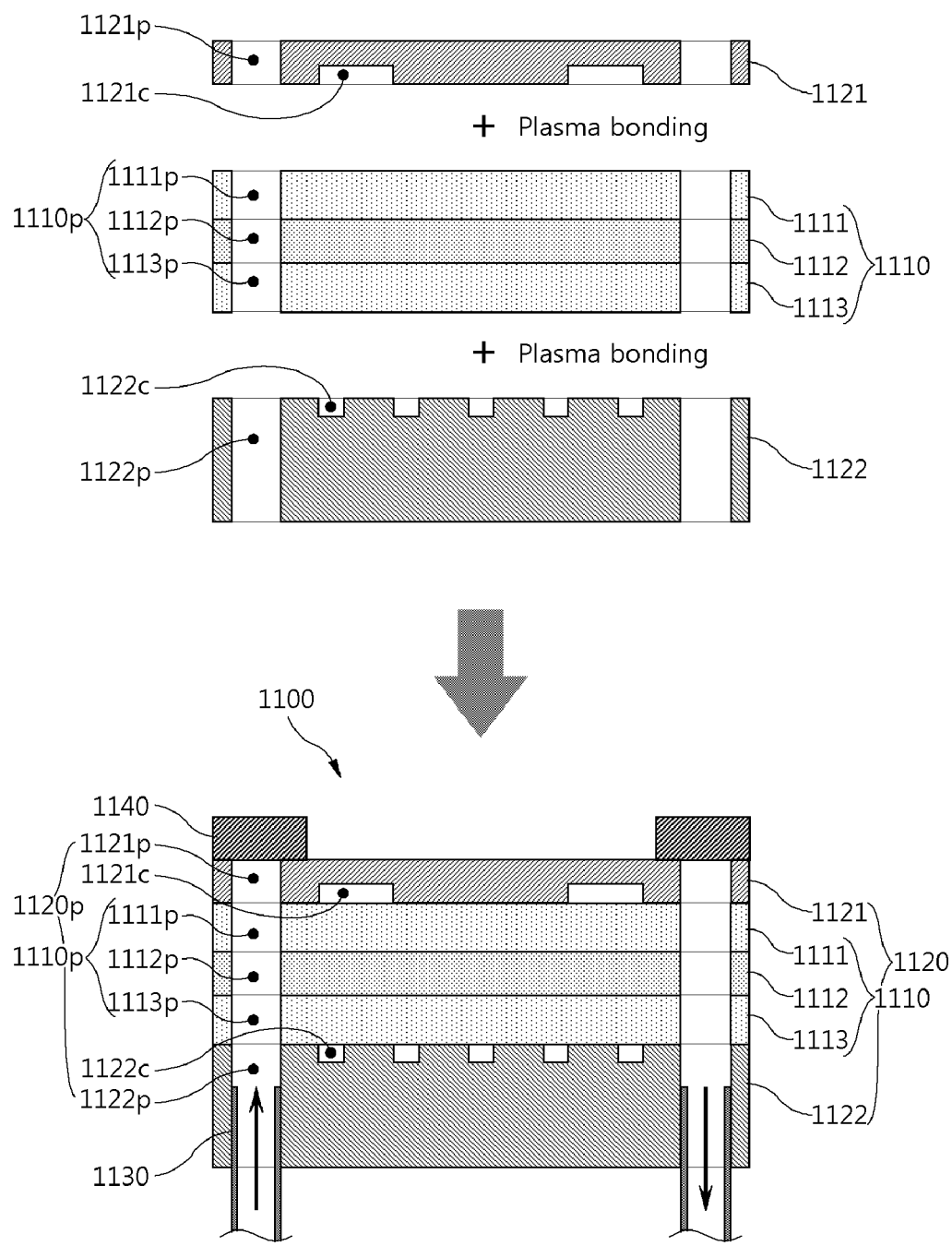
FIG. 2 is a diagram illustrating a structure of a retina simulating part of an eye phantom according to the present invention.

FIG. 2 illustrates the overall structure of the retina simulating part of the eye phantom according to the present invention. As illustrated in FIG. 2, an eye phantom 1000 according to the present invention may basically include a retina simulating part 1100 as illustrated in FIG. 2. In this case, the retina simulating part 1100 may include a multilayer film structure part 1110 that simulates the GCL, IPL, and INL among the retina structures of FIG. 1B, and a vascular layer structure part 1120 that simulates the NFL and OPL. The multilayer film structure part 1110 is formed in a shape in which multiple layers with different scattering coefficients are stacked to simulate a multilayer cell layer structure of a retina. The vascular layer structure part 1120 includes fine flow channels 1121c and 1122c, and is coupled to upper and lower surfaces of the multilayer film structure part 1110 to simulate the vascular structure of the retina. At this time, the multilayer film structure part 1110 and the vascular layer structure part 1120 may be bonded by plasma bonding as illustrated in FIG. 2.

In a state in which the blood vessel layer structure part 1120 is coupled to the upper and lower surfaces of the multilayer film structure part 1110 as described above, in order to be able to distribute a blood simulating fluid simulating blood in the fine flow channel formed in the blood vessel layer structure part 1120, a through passage through which the blood simulating fluid may pass needs to be formed in the multilayer film structure part 1110. To this end, in the multilayer film structure part 1110 is provided with a multilayer film flow passage part 1110p that is formed in the form of the through passage penetrating through the multilayer film structure part 1110 to circulate the blood simulating fluid. In addition, the blood vessel layer structure part 1120 communicates with fine flow channels 1121c and 1122c and the multilayer film flow passage part 1110p so as to distribute the blood simulating fluid, and is provided with a blood vessel layer flow passage part 1120p formed in the form of the through passage penetrating through the vascular layer structure part 1120. FIG. 2 illustrates that the blood vessel layer flow passage part 1120p is isolated from the fine flow channels 1121c and 1122c, which is only a limitation appearing because FIG. 2 is a cross-sectional view. Therefore, by appropriately designing the shapes of the fine flow channels 1121c and 1122c on a plane, the blood vessel layer flow passage part 1120p and the fine flow channels 1121c and 1122c may easily communicate with each other without limit (which will be described in more detail later).

In addition, the retina simulating part 1100 may further include a flow passage part 1130 and a sealing part 1140. The flow passage part 1130 severs to inflow or discharge the blood simulating fluid by being formed in a form of a tube connected to the blood vessel layer flow passage part 1120p formed on a lower surface of the retina simulating part to circulate the blood simulating fluid to the fine flow channel. In addition, the sealing part 1140 is formed in a form of a stopper for sealing the blood vessel layer flow passage part 1120p formed on the upper surface of the retina simulating part 1100 to prevent the blood simulating fluid from leaking the retina simulating part 1100.

In addition, the retina simulating part 1100 has been described above as simulating the NFL to the OPL, but the present invention is not limited thereto. The retina simulating part 1100 may further include a structure simulating an outer film that includes an outer nuclear layer (ONL) and an outer segment. A detailed description therefor will be provided below.

In this way, the structure that simulates the outer film is a structure similar to the multilayer film structure part 1110, and may be implemented as an outer film structure part 1150 that is further coupled to a lower surface of the vascular layer structure part 1120 coupled to the lower surface of the multilayer film structure part 1110 to simulate the outer cell layer structure of the retina. In this case, similar to the multilayer film structure part 1110, the outer film structure part 1150 may be formed in a shape in which an ONL simulating part 1151 formed in a film shape having a scattering coefficient corresponding to the outer nuclear layer (ONL) to simulate the ONL of a retinal cell layer and an outer segment simulating part 1152 formed in a film shape having a scattering coefficient corresponding to an outer segment to the outer segment of the retinal cell layer are sequentially stacked. In addition, the outer film structure part 1150 may include an ONL flow passage part formed in the form of the through passage penetrating through the ONL simulating part 1151 to circulate the blood simulating fluid to the vascular layer structure part 1120 and an outer segment flow passage part formed in the form of the through passage penetrating through the outer segment simulating part 1152 to circulate the blood simulating fluid to the vascular layer structure part 1120.

Hereinafter, the detailed structures, the OCT images, the actual photographs, the manufacturing steps, and the like of the multilayer film structure part 1110 and the blood vessel structure part 1120 will be described in more detail.

Structure of Vascular Layer Structure Part of Retina Simulating Part and Manufacturing Method First, the vascular layer structure part 1120 will be described in more detail.

Figure 3:
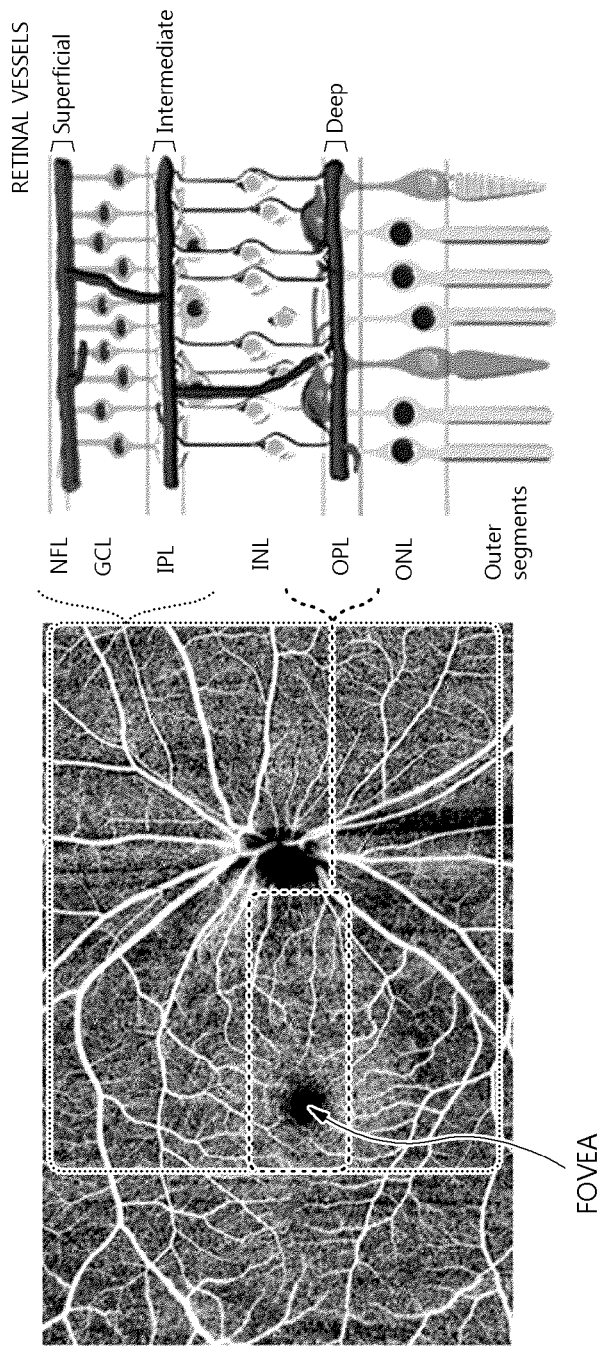
FIG. 3 is a diagram illustrating an example of an actual retinal angiography image.

FIG. 3 illustrates an example of an actual retinal angiography image. FIG. 3 illustrates that a portion represented by a minute dotted line indicates a superficial side, and generally, relatively thick blood vessels are distributed. The thick blood vessels on the superficial side are distributed in a shape in which they spread in all directions from a center as illustrated in the exemplary photograph of FIG. 3. Meanwhile, FIG. 3 illustrates that a portion represented by a thick dotted line indicates a deep side, and generally, relatively thin blood vessels are distributed. The thin blood vessels on the inner side are distributed at high density as illustrated in the exemplary photograph of FIG. 3. In particular, as illustrated in FIG. 3, a fovea in which blood vessels are not distributed at all is included in the thin blood vessel distribution area.

In the present invention, a layer made of thick blood vessels on the superficial side is simulated to an NFL simulating part 1121, and a layer made of thin blood vessels on the inner side is simulated to an OPL simulating part 1122. That is, the vascular layer structure part 1120 includes the NFL simulating part 1121 and the OPL simulating part 1122. As illustrated in FIG. 2 above, when the multilayer film structure part 1110 is formed in the shape in which the GCL/IPL/INL simulating parts 1111, 1112, and 1113 are sequentially stacked in an up-down direction, the NFL simulating part 1121 is coupled to the upper surface of the GCL simulating part 1111, that is, based on FIG. 2, so the fine flow channel formed in the NFL simulating part 1121 is formed on the lower surface. Likewise, the OPL simulating part 1122 is coupled to the INL simulating part 1113 side, that is, to the lower surface thereof based on FIG. 2, and as a result, the fine flow channel formed in the OPL simulating part 1122 is formed on the upper surface thereof.

In summary, the nerve fiber layer (NFL) simulating part 1121 is coupled to the upper surface of the multilayer film structure part by forming an NFL channel part 1121*c* in the form of the fine flow channel on the lower surface thereof to simulate the NFL of the vascular structure of the retina. In addition, the outer plexiform layer (OPL) simulating part 1122 is coupled to the lower surface of the multilayer film structure part 1110 by forming an OPL channel part 1122*c* in the form of the fine flow channel on the upper surface thereof to simulate the OPL of the vascular structure of the retina. At this time, the vascular layer structure part 1120 is formed so that the width of the NFL channel part 1121*c* is larger than that of the OPL channel part 1122*c* to simulate that the blood vessel inside the eyeball is formed thicker than the blood vessel outside the eyeball in the vascular structure of the retina.

Figure 4A:
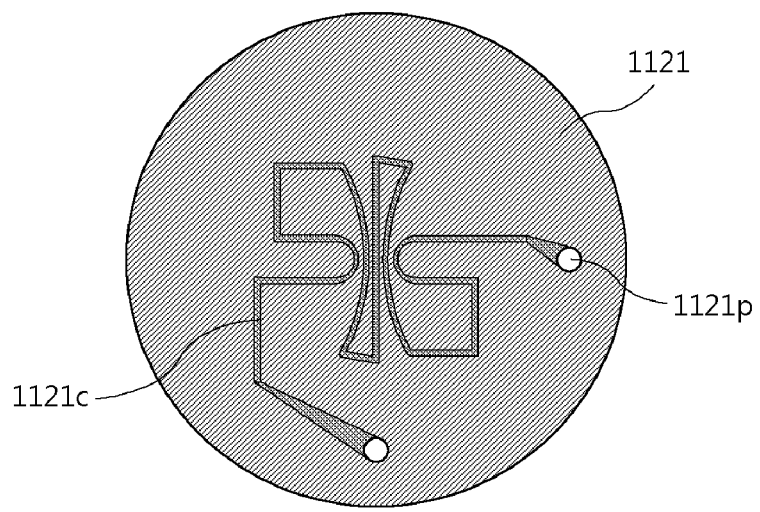
FIGS. 4A and 4B are diagrams illustrating a structure of a vascular layer structure part of the retina simulating part.
Figure 4B:
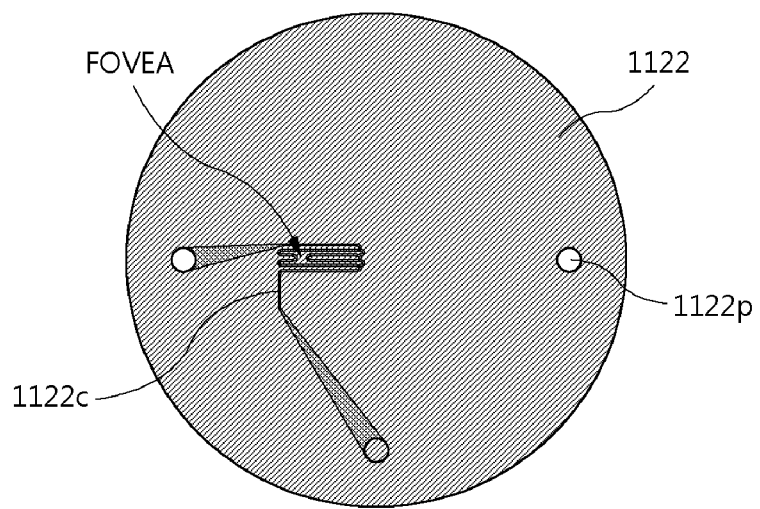

FIG. 4 exemplarily illustrates a structure of the vascular layer structure part of the retina simulating part. FIG. 4A illustrates an example of the structure of the NFL simulating part 1121, and similar to the blood vessels distributed in the actual NFL, the NFL channel part 1121*c* has a relatively large width (exemplarily, the width may be a value within the range of 100 to 200 μm) and has a structure distributed in the shape that the blood vessels spread in all directions from the center. In addition, the NFL simulating part 1121 communicates with the NFL channel part 1121*c* so as to distribute the blood simulating fluid to the NFL channel part 1121*c*, and is provided with an NFL flow passage part 1121*p* formed in the form of the through passage penetrating through the NFL simulating part 1121. Meanwhile, FIG. 4B illustrates an example of the structure of the NFL simulating part 1122, and similar to the blood vessels distributed in the actual OPL, the OPL channel part 1122*c* has a relatively small width (exemplarily, the width may be a value within the range of 10 to 50 μm), is distributed at high density and has a structure in which a fovea is formed. In addition, the OFL simulating part 1122 communicates with the OPL channel part 1122*c* so as to distribute the blood simulating fluid to the OPL channel part 1122*c*, and is provided with an OPL flow passage part 1122*p* formed in the form of the through passage penetrating through the OPL simulating part 1122.

Figure 5:
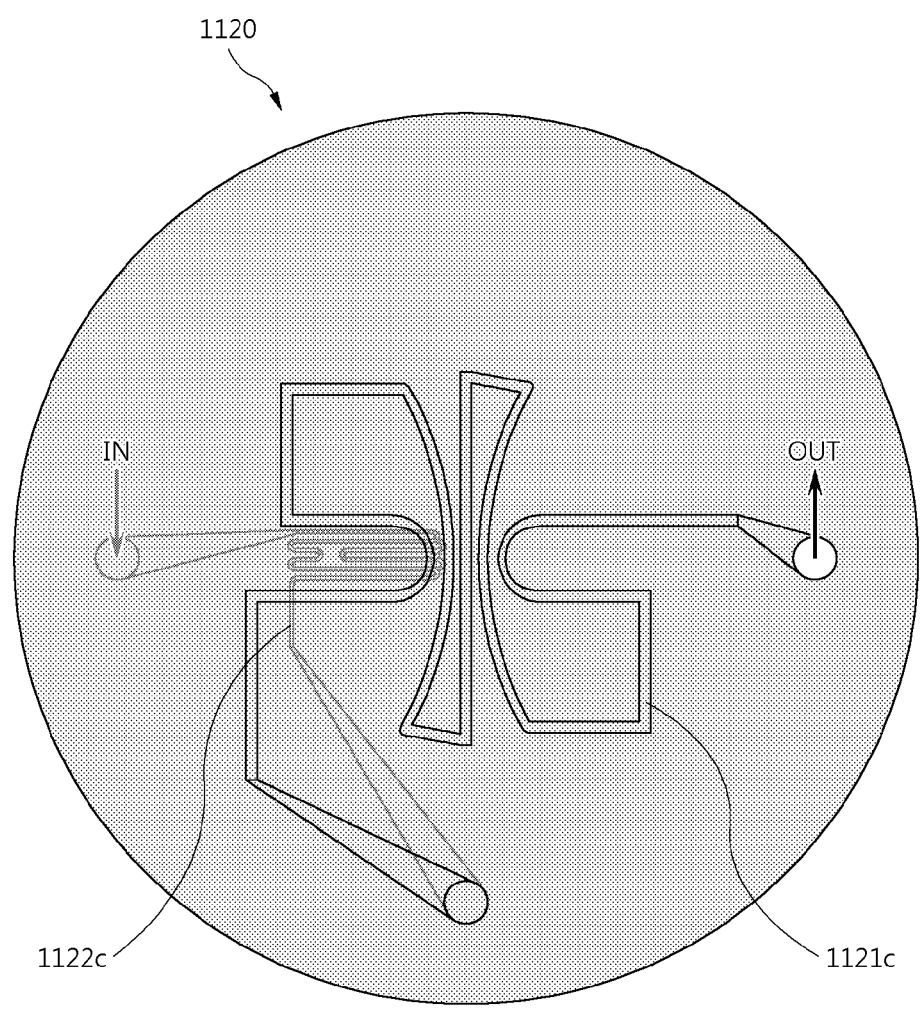
FIG. 5 is a diagram illustrating an overlapping relationship of the vascular layer structure part of the retina simulating part.

FIG. 5 exemplarily shows the overlapping relationship of the vascular layer structure part of the retina simulating part illustrated in FIG. 4, and in particular, exemplarily illustrates the overlapping relationship between the NFL flow passage part 1121*p* and the OPL flow passage part 1122*p*. As illustrated in FIG. 4A, the right/lower sides of the NFL simulating part 1121 are each provided with the NFL flow passage part 1121*p*, and the NFL channel part 1121*c* is formed in the shape in which the NFL flow passage parts 1121*p* on the right/lower sides are connected to each other. Meanwhile, as illustrated in FIG. 4B, the right/left sides of the OPL simulating part 1122 are each provided with the OPL flow passage part 1122*p*, and the OPL channel part 1122*c* is formed in the shape in which the positions corresponding to the OPL flow passage part 1122*p* on the right and the NFL flow passage part 1121*p* on the lower side are connected to each other. At this time, as illustrated in FIG. 5, when the NFL simulating part 1121 and the OPL flow passage part 1122*p* are overlapped, the NFL flow passage part 1121*p* and the OPL flow passage part 1122*p* formed on the right communicate with each other and thus the through passage is formed on the whole, but the NFL flow passage part 1121*p* formed on the lower side is stopped by the OPL simulating part 1122, and the OPL flow passage part 1122*p* formed on the left side is stopped by the NFL simulating part. However, due to the structure of the NFL channel part 1121*c* and the OPL channel part 1122*c*, the blood simulating fluid can pass through all of them, and a detailed description will be given below. First, the blood simulating fluid introduced (IN) into the OPL flow passage part 1122*p* on the left proceeds along the OPL channel part 1122*c* and reaches a position corresponding to the NFL flow passage part 1121*p* on the lower side. Then, the blood simulating fluid may be introduced into the NFL channel part 1121*c* through the NFL flow passage part 1121*p* on the lower side. Now, the blood simulating fluid introduced into the NFL flow passage part 1121*p* on the lower side proceeds along the NFL channel part 1121*c* to reach the NFL flow passage part 1121*p* on the right, and since the NFL flow passage part and the OPL flow passage part 1122p on the right communicate with each other, the blood simulating fluid may be discharged (OUT) through the OPL flow passage part 1122p on the right. The above description is only an example, and of course, contrary to the above description, the blood simulating fluid may be introduced into a portion indicated by OUT in FIG. 5 and discharged to a portion indicated by IN. That is, the point is that by properly designing the shape of the NFL channel part 1121c and the OPL channel part 1122c, and the positions of the NFL flow passage part 1121p and the OPL flow passage part 1122p, the blood simulating may be circulated through the entire path without limit.

Additionally, in the description of FIG. 5, the multilayer film structure part 1110 coupled between the NFL simulating part 1121 and the OPL simulating part 1122 has been omitted and described in order to simplify the description, but it is obvious that in the multilayer film structure part 1110, the multilayer film flow passage parts 1110p completely penetrating through the multilayer film structure part 1110 are formed at both the positions of the NFL flow passage part 1121p and the OPL flow passage part 1122p.

Figure 6A:
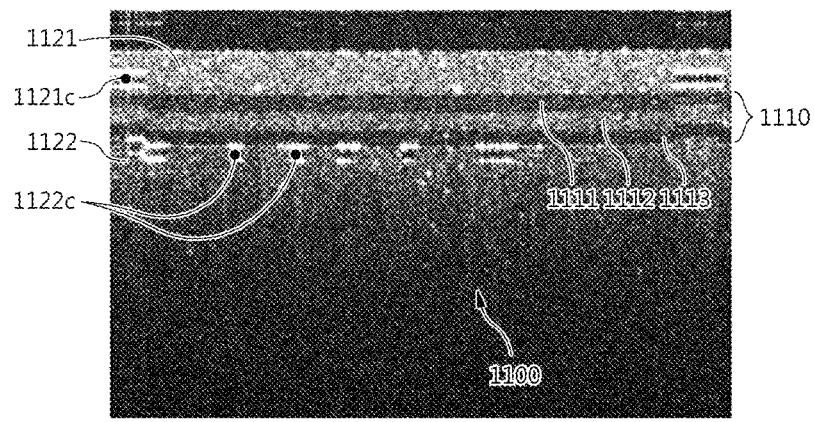
FIGS. 6A and 6B are an OCT image and an actual photograph of the retina simulating part.
Figure 6B:
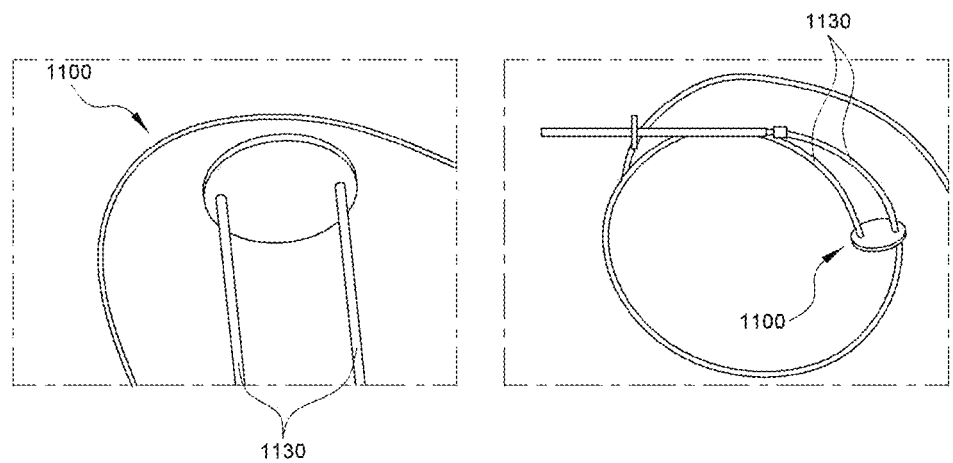

FIG. 6 illustrates an OCT image and an actual photograph of the retina simulating part. As illustrated in FIG. 6A, it is illustrated well that the NFL simulating part 1121 of the vascular layer structure part 1120 is coupled to the upper surface of the multilayer film structure part 1110, and the OPL simulating part 1122 is coupled to the lower surface of the multilayer film structure part 1110. In addition, it is illustrated well that the NFL channel part 1121c is formed on the lower surface of the NFL simulating part 1121, and the OPL channel part 1122c is formed on the upper surface of the OPL simulating part 1122. In addition, as illustrated in FIG. 6B, it is confirmed that by connecting the flow passage part 1130 to the combination of the multilayer film structure part 1110 and the vascular layer structure part 1120, the blood simulating fluid may be smoothly distributed to the fine flow channel in the vascular layer structure part 1120, that is, the NFL channel part 1121c and the OPL channel part 1122c.

FIG. 7 conceptually illustrates a process of manufacturing the vascular layer structure part of the retina simulating part. As illustrated in FIG. 7, the method for manufacturing the vascular layer structure part 1120 in the manufacturing method of the eye phantom 1000 of the present invention includes a step of irradiating light, a step of forming a reverse pattern, a step of inputting a blood vessel layer raw material, a step of stacking a substrate, a step of separating a wafer, and a step of separating a substrate.

Figure 7A:
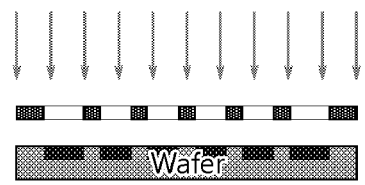
FIGS. 7A-F are diagrams illustrating a process of manufacturing the vascular layer structure part of the retina simulating part.

In the step of irradiating light, as illustrated in FIG. 7A, etching light is irradiated onto an upper surface of a wafer through a mask of a reverse pattern shape of the fine flow channel shape. That is, in the case of the NFL simulating part 1121 to be manufactured, a reverse pattern of the NFL channel part 1121c may be formed on the mask, and in the case of the OPL simulating part 1122 to be manufactured, the reverse pattern of the OPL channel part 1122c may be formed on the mask.

Figure 7B:

In the step of forming the reverse pattern, as illustrated in FIG. 7B, the light irradiation portion onto the wafer is etched away, so the reverse pattern is formed on the upper surface of the wafer.

Figure 7C:
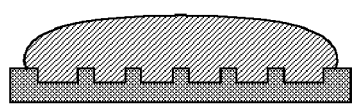

In the step of inputting the blood vessel layer raw material, as illustrated in FIG. 7C, the blood vessel layer raw material, which is the raw material of the vascular layer structure part 1120, is introduced into the reverse pattern. In this case, the blood vessel layer raw material is a mixture of a curable resin and a scattering agent. For example, the curable resin may be polydimethylsiloxane (PDMS) and the scattering agent may be $TiO_2$.

Figure 7D:
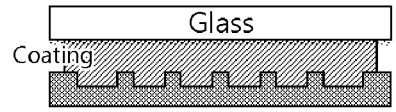

In the step of stacking the substrate, as illustrated in FIG. 7D, the substrate is stacked and pressed on the upper surface of the blood vessel layer raw material injected into the reverse pattern. As described above, since the multilayer film raw material is in a gel state before being cured as the mixture of the curable resin and the scattering agent, the substrate is stacked and pressed so that the blood vessel layer raw material may spread well throughout the wafer on which the reverse pattern is formed. On the other hand, it is preferable that the step of coating the lower surface of the substrate with a coating agent is previously performed before the step of stacking the substrate so that the blood vessel layer raw material is easily separated from the substrate in the future.

Figure 7E:
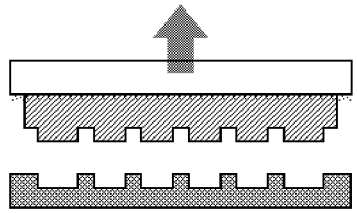

In the step of separating the wafer, as illustrated in FIG. 7E, the blood vessel layer raw material is cured in a state in which a pattern having a reverse shape to the reverse pattern is formed on the lower surface of the blood vessel layer raw material and the upper surface is adhered to the substrate, and thus is separated from the wafer. In this case, as in the above example, when the blood vessel layer raw material is mainly made of PDMS, the PDMS may be cured by being heated using a heating device because it has a property of curing by heat. Of course, if the blood vessel layer raw material is mainly made of an optical curable resin, the curing process may be appropriately determined according to the blood vessel layer raw material, such as curing by irradiating light.

Figure 7F:
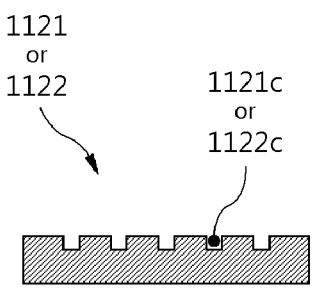

In the step of separating the substrate, as illustrated in FIG. 7F, the blood vessel layer raw material on which the fine flow channel pattern is formed is separated from the substrate. Ideally, the manufacturing of the blood vessel layer structure part 1120 may be completed by this step, but in reality, an extra portion, such as being made larger than the desired size of the blood vessel layer structure part 1120, may occur. In addition, the blood vessel layer flow passage part 1120p formed in the form of the through passage may also remain unmade in this state, and thus a part that has not yet penetrated corresponds to an extra portion. Therefore, after the step of separating the substrate, it is preferable to further perform a step of removing an extra portion in which the extra portion of the raw material of the blood vessel layer on which the fine flow channel pattern is formed is cut and removed. By doing so, the manufacturing of the blood vessel layer structure part 1120 is completed.

Structure of Multilayer film Structure Part of Retina Simulating Part and Manufacturing Method Next, the multilayer film structure part 1110 will be described in more detail.

Figure 8:
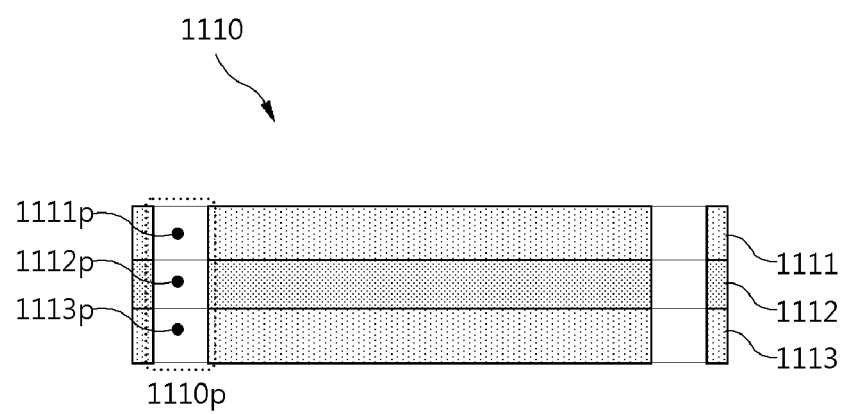
FIG. 8 is a diagram illustrating a structure of a multilayer film structure part of the retina simulating part.

FIG. 8 separately illustrates only the structure of the multilayer film structure part of the retina simulating part. As illustrated in FIG. 8, the multilayer film structure part 1110 may be formed in the shape in which the ganglion cell layer (GCL) simulating part 1111 formed in a form of a film having a scattering coefficient corresponding to GCL so as to simulate the GCL of the retinal cell layer, the inner nuclear layer (IPL) simulating part 1112 formed in a form of a film having a scattering coefficient corresponding to IPL to simulate the IPL among the cell layers of the retina, and an inner nuclear layer (INL) simulating part 1113 formed in a form of a film having a scattering coefficient corresponding to INL to simulate the INL of the retinal cell layer may be sequentially stacked. The sequential arrangement of the GCL, IPL, and INL follows the multilayer cell layer structure of the retina of the actual eyeball illustrated in FIG. 1B.

The GCL/IPL/INL simulating parts 1111, 1112, and 1113 are each provided with GCL/IPL/INL flow passage parts 1111p, 1112p, and 1113p to form the multilayer film flow passage part 1110p described above. More specifically, the GCL flow passage part 1111p is formed in the form of the through passage penetrating through the GCL simulating part 1111 to distribute the blood simulating fluid to the vascular layer structure parts 1120 provided on the upper and lower surfaces of the multilayer film structure part 1110, respectively, the IPL flow passage part 1112p is formed in the form of the through passage penetrating through the IPL simulating part 1112 to distribute the blood simulating fluid to the vascular layer structure parts 1120 provided on the upper and lower surfaces of the multilayer film structure part 1110, respectively, and the INL flow passage part 1113p is formed in the form of the through passage penetrating through the INL simulating part 1113 to distribute the blood simulating fluid to the vascular layer structure parts 1120 provided on the upper and lower surfaces of the multilayer film structure part 1110, respectively.

Figure 9A:
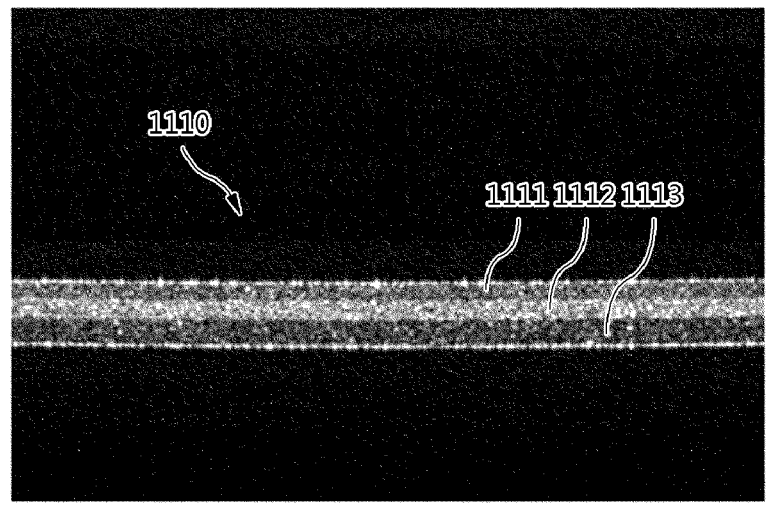
FIGS. 9A and 9B are an OCT image and an actual photograph of the multilayer film structure part of the retina simulating part.
Figure 9B:
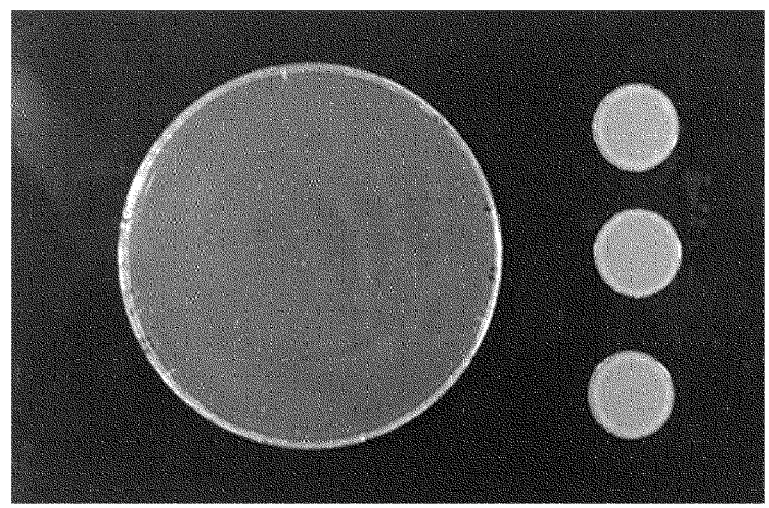

FIG. 9 illustrates an OCT image and an actual photograph of the multilayer film structure part of the retina simulating part. As illustrated in FIG. 9A, the GCL simulating part 1111, the IPL simulating part 1112, and the INL simulating part 1113 constituting the multilayer film structure part 1110 have different scattering coefficients, and therefore, appears as having different brightness in the OCT image. FIG. 9B is an actual picture of the multilayer film structure part 1110, which shows that the multilayer film structure part 1110 is actually a somewhat opaque film.

FIG. 10 conceptually illustrates a process of manufacturing the multilayer film structure part of the retina simulating part. As illustrated in FIG. 10, the method for manufacturing the multilayer film structure part 1110 among the manufacturing methods of the eye phantom 1000 of the present invention includes a step of coating an upper surface of a substrate, a step of inputting a multilayer film raw material, a step of diffusing a multilayer film raw material, a step of stopping a rotation of a substrate, and a step of curing a film.

Figure 10A:
FIGS. 10A-10F are diagrams illustrating a process of manufacturing the multilayer film structure part of the retina simulating part.

In the step of coating the upper surface of the substrate, as illustrated in FIG. 10A, the coating agent is coated on the upper surface of the substrate. The coating agent is used to facilitate separating the multilayer film structure part 1110 from the substrate after the manufacturing of the multilayer film structure part 1110 is completed.

Figure 10B:
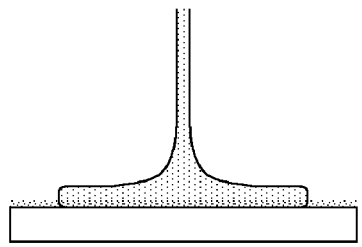

In the step of inputting the multilayer film raw material, as illustrated in FIG. 10B, the multilayer film raw material, which is the raw material of the multilayer film structure part 1110, is input to the upper surface of the substrate. In this case, the multilayer film raw material is a mixture of a curable resin and a scattering agent. For example, the curable resin may be polydimethylsiloxane (PDMS) and the scattering agent may be $TiO_2$.

Figure 10C:
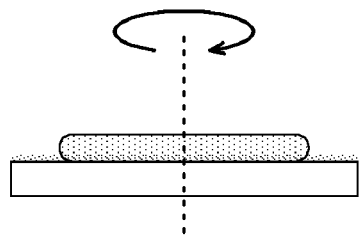

In the step of diffusing the multilayer film raw material, as illustrated in FIG. 10C, the multilayer film raw material spreads over the entire upper surface of the substrate by rotating the substrate. As described above, the multilayer film raw material, which is the mixture of the curable resin and the scattering agent, is in a gel state before being cured, and therefore easily spread by centrifugal force when the substrate rotates rapidly. In addition, the overall uniform thickness may be formed during this process. Of course, the thickness may be slightly non-uniform at the edge, but since these parts can be cut later, it is not necessary to perform work very elaborately.

Figure 10D:
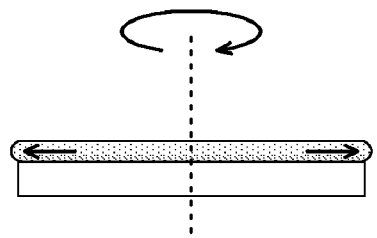

In the step of stopping the rotation of the substrate, as illustrated in FIG. 10D, when the multilayer film raw material has a predetermined thickness, the rotation of the substrate is stopped. The predetermined thickness may be appropriately determined to simulate the actual thickness values of the GCL, IPL, and INL depending on whether the layer currently being manufactured is the GCL simulating part 1111, the IPL simulating part 1112, or the INL simulating part 1113. In addition, the thickness of the multilayer film raw material varies depending on the rotation speed, rotation time, viscosity, and the like of the multilayer film raw material of the substrate. At this time, since the viscosity of the sublayer film raw material may vary little by little depending on what the currently produced layer is simulating as described above but is a predetermined value, by appropriately controlling the rotation speed and rotation time of the substrate, a layer having a desired thickness may be manufactured.

Figure 10E:
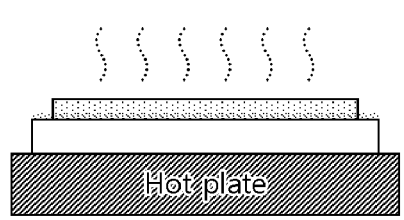

In the step of curing the film, as illustrated in FIG. 10E, the multilayer film raw material is cured. At this time, as in the above example, when the multilayer film raw material is mainly made of PDMS, the PDMS has a property to be cured by heat, and therefore, may be cured by a heating device such as a hot plate as in the example of FIG. 10E. Of course, if the multilayer film raw material is mainly made of an optical curable resin, the curing process may be appropriately determined according to the blood vessel layer raw material, such as curing by irradiating light.

Figure 10F:
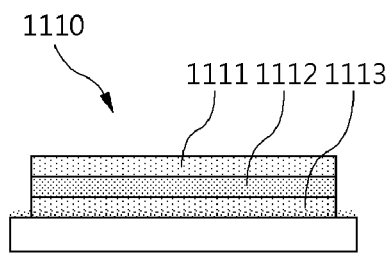

As described above, when the step of inputting the multilayer film raw material, the step of diffusing the multilayer film raw material, the step of stopping the rotation of the substrate, and the step of curing the film are performed once, a single film is manufactured. These steps are sequentially repeated, so as shown in FIG. 10F, a laminate of multiple layers may be formed on the upper surface of the substrate. At this time, as described above, the ratio of the curable resin and scattering agent of the multilayer film raw material may be appropriately determined depending on whether the layer currently being manufactured is the GCL simulating part 1111, the IPL simulating part 1112, or the INL simulating part 1113, so a laminate of multiple layers having different scattering coefficients may be manufactured. The manufacturing of the multilayer film structure part 1110 is completed by properly cutting the laminate of the multiple layers having different scattering coefficients and piercing the through passage at appropriate position to form the multilayer film flow passage part 1110p.

Additionally, the outer film structure part 1150 may also be manufactured by applying the method for manufacturing the multilayer film structure part 1110 as it is. Accordingly, the method for manufacturing the outer film structure part 1150 is not separately described.

Overall Structure of Eye Phantom

As described above, the retina simulating part in the conventional eye phantom has only the shape of the multilayer film structure that simulates only the multilayer cell layer structure of the retina. However, in the eye phantom 1000 of the present invention, the retina simulating part 1100 is formed in a form in which the vascular layer structure part 1120 formed with the fine flow channel is coupled to the upper and lower surfaces of the multilayer film structure part 1110 to distribute the blood simulating fluid to the fine flow channel, so the retina simulating part 1100 is formed to simulate not only the multilayer cell layer structure of the retina but also the vascular structure and blood flow of the retina. In addition, as described above, the retina simulating part 1100 may further include the outer film structure part 1150 that is further coupled to the lower surface of the vascular layer structure part 1120 coupled to the lower surface of the multilayer film structure part 1110 to simulate the outer cell layer structure of the retina. In this case, the outer film structure part 1150 may be provided with the outer film flow passage part formed in the form of the through passage penetrating through the outer film structure part 1150 to circulate the blood simulation fluid, and the flow passage part 1130 may communicate with the blood vessel layer flow passage part 1120p through the outer film flow passage part. In addition, the eye phantom 1000 according to the present invention may further include a lens part 1200 and a housing part 1300 in order to more closely simulate the eyeball.

Figure 11:
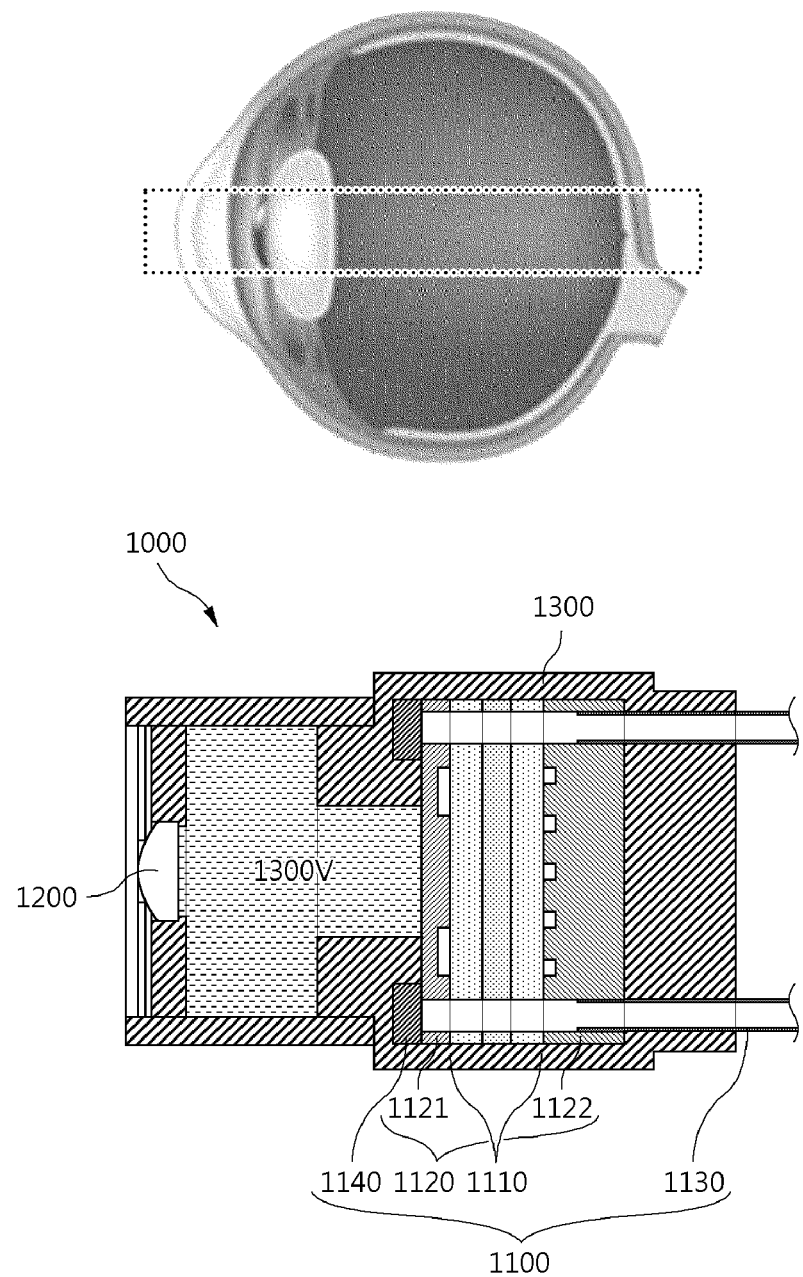
FIG. 11 is a diagram illustrating a structure of an eye phantom according to the present invention.

FIG. 11 illustrates a structure of the eye phantom according to the present invention. As illustrated in FIG. 11, the lens part 1200 included in the eye phantom 1000 includes at least one lens to simulate a crystalline lens of the eyeball. In FIG. 11, the lens part 1200 is illustrated as including one lens, but the lens part 1200 may be constituted by a laminate of a plurality of lenses, if necessary. The retina simulating part 1100 is spaced apart from the lens part 1200 so that the upper surface (that is, the NFL simulating part 1121 side) faces the lens part 1200 on the axis of the lens part 1200. In addition, the housing part 1300 has a shape supporting the lens part 1200 on one side thereof and the retina simulating part 1100 on the other side thereof. At this time, the eye phantom 1000 is provided with an accommodation space 1300V in which a vitreous body simulation fluid is accommodated between the lens part 1200 and the retina simulating part 1100 in the housing part 1300 so as to simulate the vitreous body of the eyeball. In this case, the vitreous body simulation fluid may be water as an example. It may be considered that the eye phantom 1000 made in this way simulates the same part as indicated by the dotted square in the actual eyeball drawing on the upper side of FIG. 11.

Figure 12:
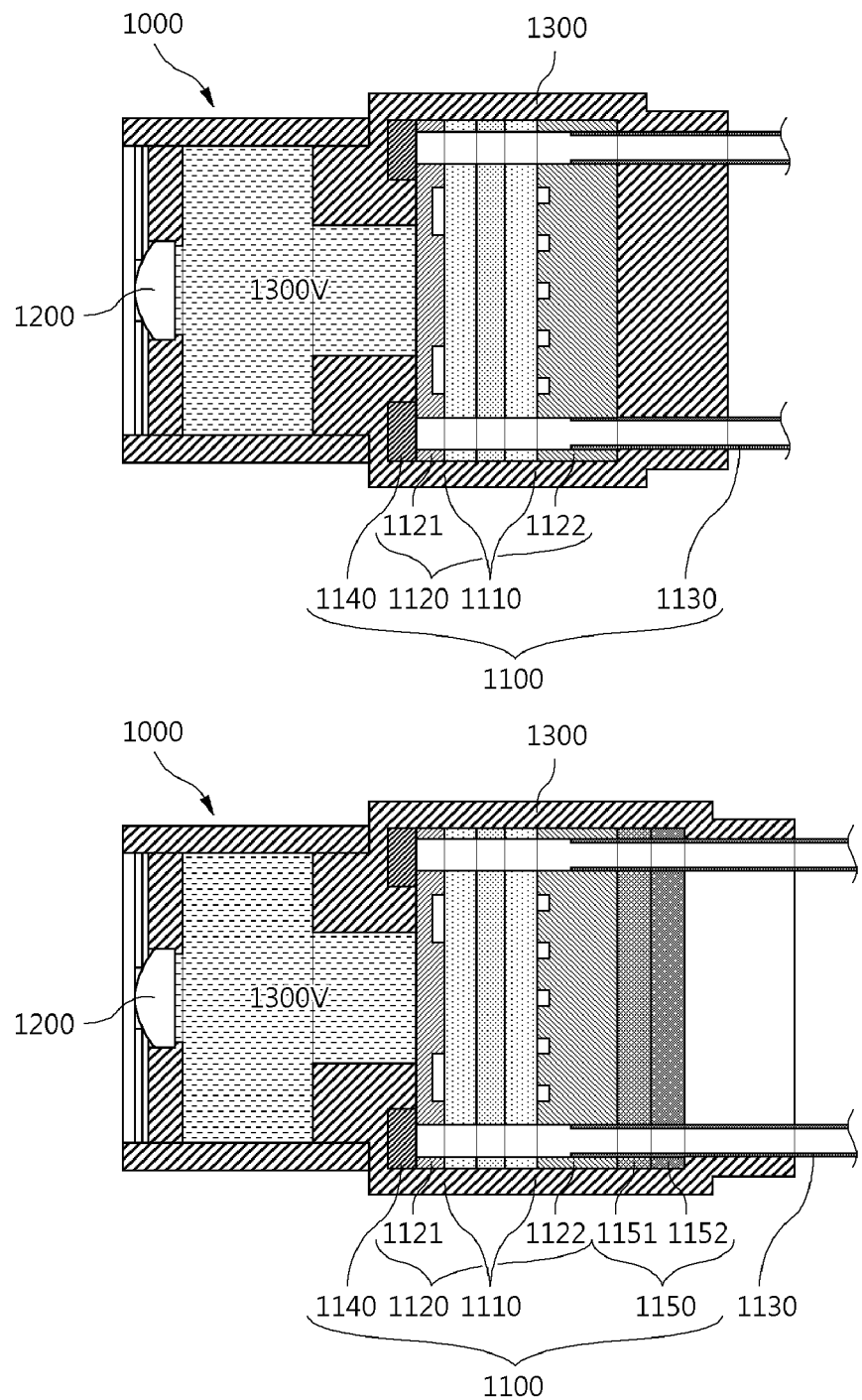
FIG. 12 is a diagram illustrating various embodiments of the structure of the eye phantom according to the present invention.

FIG. 12 illustrates a comparison between the case where the retina simulating part 1100 does not include the outer film structure part 1150 (the same as the upper view and the lower view of FIG. 11) and the case (the lower view) where the retina simulating part 1100 includes the outer film structure part 1150. As illustrated above, except that the outer film structure part 1150 is further stacked on the lower surface of the retina simulating part 1100 (that is, the OPL simulating part 1122 side) on the axis of the lens part 1200, the structure is the same as before, the redundant description thereof will be omitted.

FIG. 13 illustrates an actual photograph of the eye phantom according to the present invention. As illustrated, in the eye phantom 1000, it is preferable that the flow passage part 1130 is provided with the flow rate control unit to control the flow rate of the blood simulating fluid flowing into and out of the retina simulating part 1100.

The present invention is not limited to the above-mentioned exemplary embodiments but may be variously applied, and may be variously modified by those skilled in the art to which the present invention pertains without departing from the gist of the present invention claimed in the claims.

INDUSTRIAL APPLICABILITY

According to the present invention, as described above, the eye phantom 1000 may include various shapes of fine fluid channel structures corresponding to the vascular structure formed in the actual retina, thereby simulating even the vascular structure and blood flow of a retina so as to be more similar to an actual retinal structure than a conventional eye phantom. Therefore, according to the present invention, the eye phantom 1000 is applied to the fifth generation OCT development process equipped with the function of acquiring the angiography image from the OCT image, thereby accurately evaluating the performance of the equipment under development.

The invention claimed is:
1. An eye phantom, comprising:
    a retina simulating part, the retina simulating part including a multilayer film structure part that is formed in a shape in which multiple layers with different scattering coefficients are stacked to simulate a multilayer cell layer structure of a retina; and
    a vascular layer structure part that includes a fine flow channel to simulate a vascular structure of the retina and is coupled to an upper surface and a lower surface of the multilayer film structure part, wherein the vascular layer structure part includes:
    a nerve fiber layer (NFL) simulating part that is coupled to the upper surface of the multilayer film structure part by forming an NFL channel part in a form of the fine flow channel on the lower surface thereof to simulate the NFL of the vascular structure of the retina; and
    an outer plexiform layer (OPL) simulating part that is coupled to the lower surface of the multilayer film structure part by forming an OPL channel part in the form of the fine flow channel on the upper surface thereof to simulate the OPL of the vascular structure of the retina.
2. The eye phantom of claim 1, wherein the vascular layer structure part is formed so that a width of the NFL channel part is formed larger than that of the OPL channel part to simulate that a blood vessel inside an eyeball is formed thicker than that outside the eyeball in the vascular structure of the retina.
3. The eye phantom of claim 2, wherein the NFL channel part has a width within a range of 100 to 200 μm.
4. The eye phantom of claim 2, wherein the OPL channel part has a width within a range of 10 to 50 μm.
5. The eye phantom of claim 1, wherein the vascular layer structure part includes:
    an NFL flow passage part that communicates with the NFL channel part to circulate a blood simulating fluid through the NFL channel part and is formed in a form of a through passage penetrating through the NFL simulating part; and
    an OPL flow passage part that communicates with the OPL channel part to circulate the blood simulating fluid to the OPL channel part and is formed in a form of a through passage penetrating through the OPL simulating part.
6. The eye phantom of claim 1, wherein the multilayer film structure part is formed in a shape in which a ganglion cell layer (GCL) simulating part is formed in a form of a film having a scattering coefficient corresponding to GCL to simulate the GCL among cell layers of the retina,
    wherein an inner plexiform layer (IPL) simulating part is formed in a form of a film having a scattering coefficient corresponding to IPL to simulate the IPL of the retinal cell layer, and
    wherein an inner nuclear layer (INL) simulating part is formed in a form of a film having a scattering coefficient corresponding to INL to simulate the IPL of the retinal cell layer are sequentially stacked.

7. The eye phantom of claim 6, wherein the multilayer film structure part includes:
- a GCL flow passage part that is formed in a form of a through passage penetrating through the GCL simulating part to circulate a blood simulating fluid to the vascular layer structure parts provided on each of the upper and lower surfaces of the multilayer film structure part;
- an IPL flow passage part that is formed in a form of a through passage penetrating through the IPL simulating part to circulate a blood simulating fluid to the vascular layer structure parts provided on each of the upper and lower surfaces of the multilayer film structure part; and
- an INL flow passage part that is formed in a form of a through passage penetrating through the INL simulating part to circulate a blood simulating fluid to the vascular layer structure parts provided on each of the upper and lower surfaces of the multilayer film structure part.

8. The eye phantom of claim 1, wherein the retina simulating part further includes an outer film structure part that is further coupled to a lower surface of the vascular layer structure part coupled to the lower surface of the multilayer film structure part to simulate an outer cell layer structure of the retina.

9. The eye phantom of claim 8, wherein the outer film structure part is formed in a shape in which an outer nuclear layer (ONL) simulating part is formed in a form of a film having a scattering coefficient corresponding to ONL to simulate the ONL of the retinal cell layer, and
- wherein an outer segment simulating part is formed in a form of a film having a scattering coefficient corresponding to an outer segment to simulate the outer segment of the retinal cell layer are sequentially stacked.

10. The eye phantom of claim 9, wherein the outer film structure part includes:
- an ONL flow passage part that is formed in a form of a through passage penetrating through the ONL simulating part to circulate a blood simulating fluid to the vascular layer structure part, and
- an outer segment flow passage part that is formed in a form of a through passage penetrating through the outer segment simulating part to circulate the blood simulating fluid to the vascular layer structure part.

11. The eye phantom of claim 1, wherein the retina simulating part further includes:
- a multilayer film flow passage part that is formed on the multilayer film structure part in a form of a through passage penetrating through the multilayer film structure part to circulate a blood simulating fluid and a blood vessel layer flow passage part that is formed on the vascular layer structure part in a form of a through passage communicating with the fine flow channel and the multilayer film flow passage part and penetrating through the vascular layer structure part;
- a flow passage part that inflows or discharges a blood simulating fluid by being formed in a form of a tube connected to the blood vessel layer flow passage part formed on a lower surface of the retina simulating part to circulate the blood simulating fluid to the fine flow channel; and
- a sealing part that is formed in a form of a stopper that seals the blood vessel layer flow passage part formed on an upper surface of the retina simulating part to prevent the blood simulating fluid from leaking the retina simulating part.

12. The eye phantom of claim 11, wherein the retina simulating part further includes:
- an outer film structure part that is further coupled to a lower surface of the vascular layer structure part coupled to the lower surface of the multilayer film structure part to simulate an outer cell layer structure of the retina;
- an outer film flow passage part formed in a form of a through passage penetrating through the outer film structure part is formed in the outer film structure part to circulate a blood simulating fluid; and
- the flow passage part communicates with the blood vessel layer flow passage part through the outer film flow passage part.

13. The eye phantom of claim 11, further comprising:
- a lens part that includes at least one lens to simulate a crystalline lens of an eyeball;
- wherein the retina simulating part is spaced apart from the lens part so that an upper surface faces toward the lens part on an axis of the lens part; and
- a housing part that has the lens part supported on one side thereof and the retina simulating part supported on the other side thereof.

14. The eye phantom of claim 13, wherein an accommodation space in which a vitreous body simulation fluid is accommodated is formed between the lens part and the retina simulating part in the housing part to simulate a vitreous body of the eyeball.

15. The eye phantom of claim 13, further comprising:
- a flow rate control unit that is provided in the flow passage part to control a flow rate of the blood simulating fluid that flows into and is discharged from the retina simulating part.

16. A manufacturing method of the eye phantom of claim 1 for manufacturing the vascular layer structure part, comprising:
- irradiating etching light onto an upper surface of a wafer through a mask having a reverse pattern shape of the fine flow channel shape;
- forming a reverse pattern on the upper surface of the wafer by etching and removing the light irradiated portion on the wafer;
- inputting a blood vessel layer raw material, which is a raw material of the vascular layer structure part, into the reverse pattern;
- stacking and pressing a substrate on an upper surface of the blood vessel layer raw material input into the reverse pattern;
- separating, from the wafer, the blood vessel layer raw material cured in a state in which a pattern having a reverse shape to the reverse pattern is formed on a lower surface of the blood vessel layer raw material, and the upper surface thereof adheres to the substrate; and
- separating the blood vessel layer raw material on which the fine flow channel pattern is formed from the substrate.

17. The manufacturing method of the eye phantom of claim 16, further comprising:
- before the stacking and pressing of the substrate,
- coating a coating agent on a lower surface of the substrate to easily separate the blood vessel layer raw material from the substrate in the separating of the blood vessel layer raw material from the substrate.

18. The manufacturing method of the eye phantom of claim 16, further comprising:
after the separating of the blood vessel layer raw material from the substrate,
cutting and removing an extra portion of the blood vessel layer raw material on which the fine flow channel pattern is formed.

19. The manufacturing method of the eye phantom of claim 16, wherein the blood vessel layer raw material is a mixture of a curable resin and a scattering agent.

20. The manufacturing method of the eye phantom of claim 19, wherein the curable resin is polydimethylsiloxane (PDMS).

21. The manufacturing method of the eye phantom of claim 19, wherein the scattering agent is $TiO_2$.

22. A manufacturing method of the eye phantom of claim 1 for manufacturing the multilayer film structure part, comprising:
coating a coating agent on an upper surface of a substrate;
inputting a multilayer film raw material, which is a raw material of the multilayer film structure part, into the upper surface of the substrate;
diffusing the multilayer film raw material into the whole upper surface of the substrate by rotating the substrate;
stopping the rotation of the substrate when the multilayer film raw material forms a predetermined thickness; and
curing the multilayer film raw material.

23. The manufacturing method of the eye phantom of claim 22, further comprising:
forming a laminate of multiple layers having different scattering coefficients on the upper surface of the substrate by repeatedly forming the multilayer film the inputting of the multilayer film raw material, the diffusing of the multilayer film raw material, the stopping of the rotation of the substrate, and the curing of the film.

24. The manufacturing method of the eye phantom of claim 22, wherein the multilayer film raw material is a mixture of a curable resin and a scattering agent.

25. The manufacturing method of the eye phantom of claim 24, wherein the curable resin is polydimethylsiloxane (PDMS).

26. The manufacturing method of an eye phantom of claim 24, wherein the scattering agent is $TiO_2$.

* * * * *